(12) United States Patent
Kremerman (10) Patent No.: US 10,279,281 B2
(45) Date of Patent: May 7, 2019

(54) BULBOUS FRACTIONAL COLLECTOR IN DISTILLATION HEAD

(71) Applicant: Elliot Kremerman, Scotts Valley, CA (US)

(72) Inventor: Elliot Kremerman, Scotts Valley, CA (US)

( * ) Notice: Subject to any disclaimer, the term of this patent is extended or adjusted under 35 U.S.C. 154(b) by 0 days.

(21) Appl. No.: 16/129,076

(22) Filed: Sep. 12, 2018

(65) Prior Publication Data

US 2019/0009188 A1 Jan. 10, 2019

(51) Int. Cl.
| | | |
|---|---|---|
| *B01D 5/00* | (2006.01) |
| *B01D 3/14* | (2006.01) |
| *B01D 3/10* | (2006.01) |
| *G01N 1/22* | (2006.01) |
| *B01D 3/32* | (2006.01) |
| *G01N 25/14* | (2006.01) |
| *F28B 1/02* | (2006.01) |
| *B01D 11/02* | (2006.01) |

(52) U.S. Cl.
CPC ............ *B01D 5/009* (2013.01); *B01D 3/108* (2013.01); *B01D 3/143* (2013.01); *B01D 5/006* (2013.01); *B01D 3/32* (2013.01); *B01D 5/0063* (2013.01); *B01D 11/0296* (2013.01); *F28B 1/02* (2013.01); *G01N 25/145* (2013.01); *G01N 2001/2282* (2013.01)

(58) Field of Classification Search
CPC .......... B01D 3/108; B01D 3/143; B01D 3/32; B01D 5/0063; B01D 5/009; B01D 3/04; B01D 5/006; F28B 1/02; G01N 2001/2282; G01N 25/145
See application file for complete search history.

(56) References Cited

U.S. PATENT DOCUMENTS

| | | |
|---|---|---|
| 1,418,691 A | 6/1922 | Anders |
| 2,383,377 A | 8/1945 | Evans |
| 2,427,142 A | 9/1947 | Hornbacher |
| 2,468,872 A | 5/1949 | Goldsbarry |
| 2,701,789 A | 2/1955 | White |
| 3,240,682 A | 3/1966 | Gordon |
| 3,334,025 A | 8/1967 | Reid |

(Continued)

OTHER PUBLICATIONS

Applicant Disclosure of the subject matter on "Instagram", Nov. 6, 2017.

(Continued)

*Primary Examiner* — Youngsul Jeong
*Assistant Examiner* — Gabriel E Gitman
(74) *Attorney, Agent, or Firm* — Michael J. Feigin, Esq.; Feigin and Fridman (57) ABSTRACT

A distillation head with fraction collector is disclosed. In embodiments thereof, the fraction collector has a bottom portal which is raised up from the floor or bottom thereof. Fractions which condense fall to the floor and a lip of the bottom portal, raised from the floor of the fraction collector, prevents condensed fractions from falling downwards through a path of entry. Rather, condensed fractions exit in liquid form out a side portal. The fraction collector further has side walls which are, in embodiments, partially vertical and/or partially curvilinear and/or partially bulbous. The distillation head also can have a top portal through which a vacuum can be applied.

16 Claims, 10 Drawing Sheets

(56) References Cited

U.S. PATENT DOCUMENTS

| | | | |
|---|---|---|---|
| 3,334,966 A | | 8/1967 | Shepherd |
| 3,397,115 A | * | 8/1968 | Tobey ................ B01D 11/0219 |
| | | | 202/169 |
| 3,607,662 A | | 9/1971 | Glover |
| 3,736,234 A | * | 5/1973 | Miyamoto ........... B01D 5/0006 |
| | | | 122/491 |
| 3,812,010 A | | 5/1974 | Nitsch |
| 3,837,830 A | | 9/1974 | Eberhart |
| 4,081,331 A | * | 3/1978 | Weiss ...................... B01D 3/00 |
| | | | 202/181 |
| 5,076,349 A | * | 12/1991 | Kadono ............... B01D 5/0012 |
| | | | 165/104.19 |
| 5,164,049 A | | 11/1992 | Clark |
| 5,354,428 A | | 10/1994 | Clark |
| 5,873,980 A | | 2/1999 | Young |
| 5,961,787 A | * | 10/1999 | Persson ............. B01D 11/0219 |
| | | | 202/168 |
| 9,682,331 B2 | | 6/2017 | Kremerman |
| 9,895,626 B2 | | 2/2018 | Kremerman |
| 9,895,627 B2 | | 2/2018 | Kremerman |
| 10,029,188 B2 | | 7/2018 | Kremerman |
| 2015/0367250 A1 | * | 12/2015 | Alstin .................. B01D 5/0051 |
| | | | 202/170 |

OTHER PUBLICATIONS

Greenleaf Scientific Disclosure of the subject matter obtained directly or indirectly from the inventor, accessed Aug. 6, 2018.

\* cited by examiner

BULBOUS FRACTIONAL COLLECTOR IN DISTILLATION HEAD

FIELD OF THE DISCLOSED TECHNOLOGY

The disclosed technology relates generally to distillation and, more specifically, to distillation equipment with a fraction collector.

BACKGROUND OF THE DISCLOSED TECHNOLOGY

Distillation or fractional distillation is carried out by heating a solid or liquid and removing gaseous vapors that are expelled therefrom. This can be done while raising the temperature, as each compound boils at a different temperature. However, when working with small amounts of starting raw material or items which have close boiling points, this can be difficult, as multiple compounds get removed simultaneously. Further, a problem can arise when the temperature throughout the distillation equipment is not constant, and some of the vapor re-condenses before being evacuated from a distillation chamber.

Thus, there is a need to find a way to distill with greater efficiency and separation of compounds, while preventing vapors from re-condensing back into the product being distilled.

SUMMARY OF THE DISCLOSED TECHNOLOGY

The terms "top" and "bottom" refer to compared to a direction of a pull of gravity. The "bottom" point is that which is closed towards the direction of pull of gravity (such as the center of the Earth) whereas the "top" point is furthest therefrom such that gravity pulls from high to low. Thus, a distillation head of embodiments of the disclosed technology has a vertical tube extending into a fraction collector. The fraction collector is a part of glassware (or other material) which an interior space which is entered into and extends below an upper most extent of a vertical tube, and a side exit portal aligned with a bottom most extend of the fraction collector and being lower than an upper most extent of the vertical tube.

The fraction collector has a side portal and/or exit region attached to a condenser or other device which can form a unitary or separate structure with/to the distillation head. An "exit region" is defined as a portion with a bottom side extending past vertical extends of glassware between the interior space of the fraction collector and another element of the glassware; the "exit region" can be a single vertical plane or have a horizontal extent. The condenser, in embodiments of the disclosed technology, is external to the fraction collector and connects thereto by way of the exit region there-between. The exit region can be perpendicular to the vertical tube. The fraction collector is free from obstruction (unencumbered) other than the vertical tube forming a shelf (top edge of the vertical tube) therein.

The fraction collector, in embodiments of the disclosed technology, has vertical side walls, the vertical side walls interrupted by a section of curvilinear side walls. The curvilinear side walls, in some embodiments of the disclosed technology, are within a top quarter of a length of the vertical side walls (of the fraction collector). The fraction collector can further have a top portal, being a top vacuum portal which is open to the outside of the distillation head.

The fraction collector, in embodiments of the disclosed technology, has bulbous side walls which curvilinearly extend into the vertical tube at a bottom side thereof and a to vacuum portal at a top side thereof. The vertical tube extends into the fraction collector less than 25% by height in some embodiments. "Curvilinear" is defined as "being in a continuous line which curves." "Bulbous" is defined as "having a bulging section being wider than narrower adjacent and continuous sections."

Described another way, a fraction collector of embodiments of the disclosed technology has a horizontal bottom side, a combination of a vertical and curvilinear side wall, a top portal, and a bottom side. An interior space of the fraction collector is defined by a space between the bottom side, the side wall, and the top portal. A vertical tube extends past the bottom side into the interior space of the fraction collector.

A side exit portal whose bottom most extent is at the bottom side of the fraction collector can be adjacent to/join with the interior space of the fraction collector. The vertical tube and the top portal have, in embodiments of the disclosed technology, a same circumference and are aligned horizontally with each other. That is, the bulbous fraction collector "interrupts" an otherwise continuous vertical channel extending through a vertical tube both below and above the fraction collector.

Said yet another way, a fraction collector of embodiments of the disclosed technology forms a bulbous section between a vertical tube entering into a bottom side of the bulbous section and a top portal, the top portal aligned with the vertical tube. The top portal, in some embodiments, is formed from a piece of glass which is continuous with the bulbous section. A bottom side of the bulbous section curves into and is continuous with (defined as "connected thereto without a break or space") the vertical tube, the vertical tube extending both upwards and downwards past a point where the bulbous section meets the vertical tube.

A side exit portal cuts into the bulbous section and has a bottom side which is horizontal and continuous with the bottom side of the fraction collector in embodiments of the disclosed technology. The vertical tube extends into the bulbous section at least 10% and no more than 40%, by height thereof in some embodiments of the disclosed technology.

A "distillation head" is defined as a device in which vapors of a solid, liquid, or combination solid and liquid product to be distilled move upwards therein before exiting into a distribution adapter or condenser. "Distillate" refers to and is defined as the vapor, liquid, or combination thereof which exits, by way of the fraction collector, from the distillation head and is ultimately fractionally distilled into component parts, each component part having different physical properties such as a different boiling point. For purposes of this disclosure, material packing is synonymous with "Raschig rings" and are defined as inert packing material which stays structurally intact through changes in temperature and passage of vapors there-around during fractional distillation. Interior extending flanges fixedly attached to an inside of the vertical tube can also be used in embodiments of the disclosed technology.

Any device or step to a method described in this disclosure can comprise, or consist of, that which it is a part of, or the parts which make up the device or step. The term "and/or" is inclusive of the items which it joins linguistically and each item by itself. Any element or described portion of the devices shown can be "substantially" as such, if used in

DETAILED DESCRIPTION OF EMBODIMENTS OF THE DISCLOSED TECHNOLOGY

The distillation head of embodiments of the disclosed technology has a flat collecting surface 360 degrees around an upward extending tube. A prior version having some of the elements of this patent is found in U.S. Pat. No. 10,029,188 to the same inventor. However, the prior version has a distillation key and larger collecting surface. The present technology has a fraction collector formed from a cylindrical base and mid-region with narrowing top side. The fraction collector is entirely open within its outer walls but for the lower tube entering therein the area contained within the outer walls. This allows the fraction collector of the present technology to be used with shorter distillation heads lacking a distillation key or the like of the prior versions.

The tube entering into the fraction collector creates a shelf at the top edge of the tube and circumferential lip just beneath the shelf where vapors condense. The shelf is equal height/joins with a side exit portal. In this manner, hot vapors extend up the tube and when the vapors cool and become liquid or solid they do so to the side of the tube and fall to the shelf where they then exit rather than falling back down the tube.

Thus, the shelf is 360 degree "collection dish" to the exterior of a vertical distillation tube and near the top edge thereof (within 10% of a distance from top of the vertical tube). A vacuum to pull discharge is at the top side of the distillation head, and in embodiments, is only at the top side thereof. Having a vacuum at the top side prevents condensed fractions in liquid form from being sucked into the vacuum as the vacuum is calibrated, in embodiments of the disclosed technology, to be less strong than what is able to pull liquid from the fraction collector up through a vacuum placed a top side of the distillation head. Purity of the distillate fractions has also been increased with the present technology.

Figure 1:
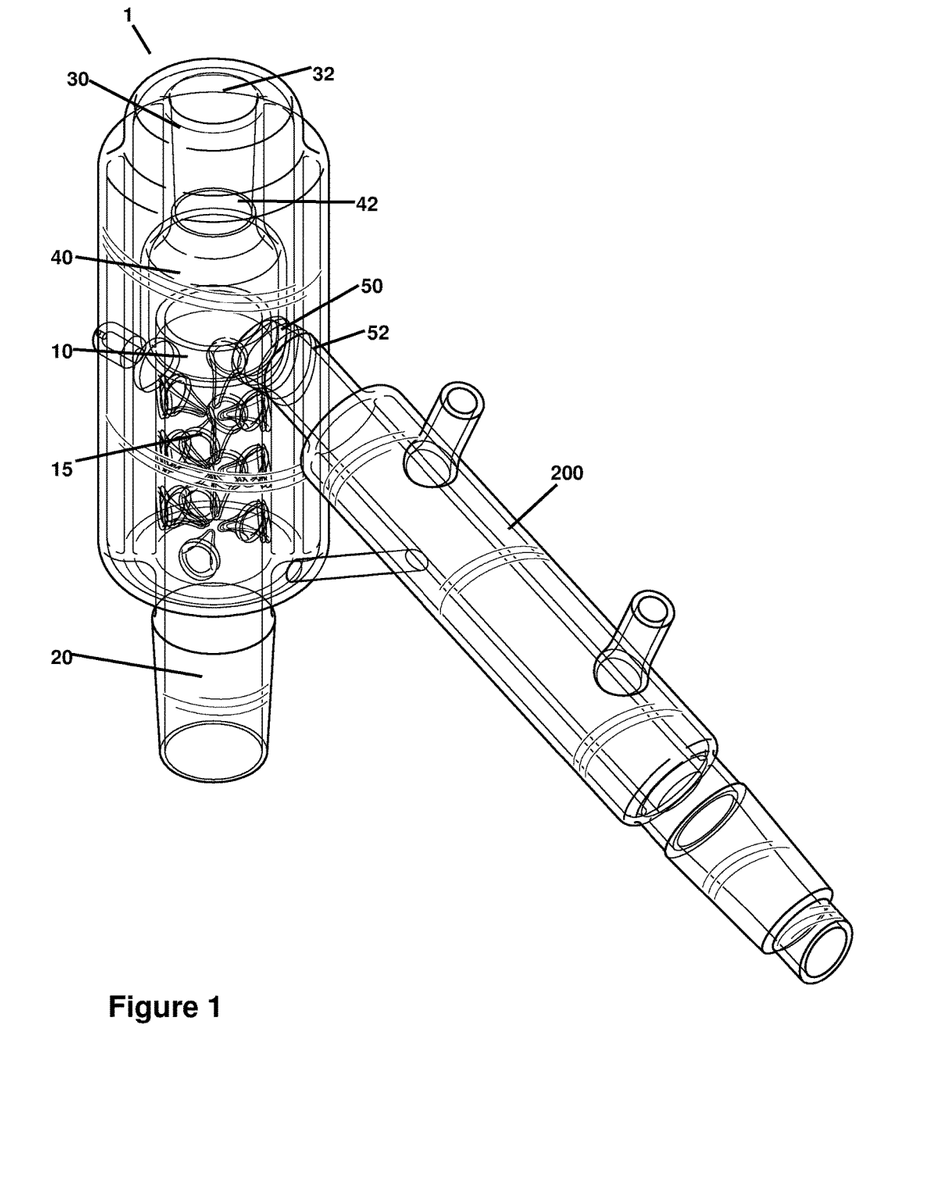
FIG. 1 shows a top and side perspective view of a distillation head.
Figure 2:
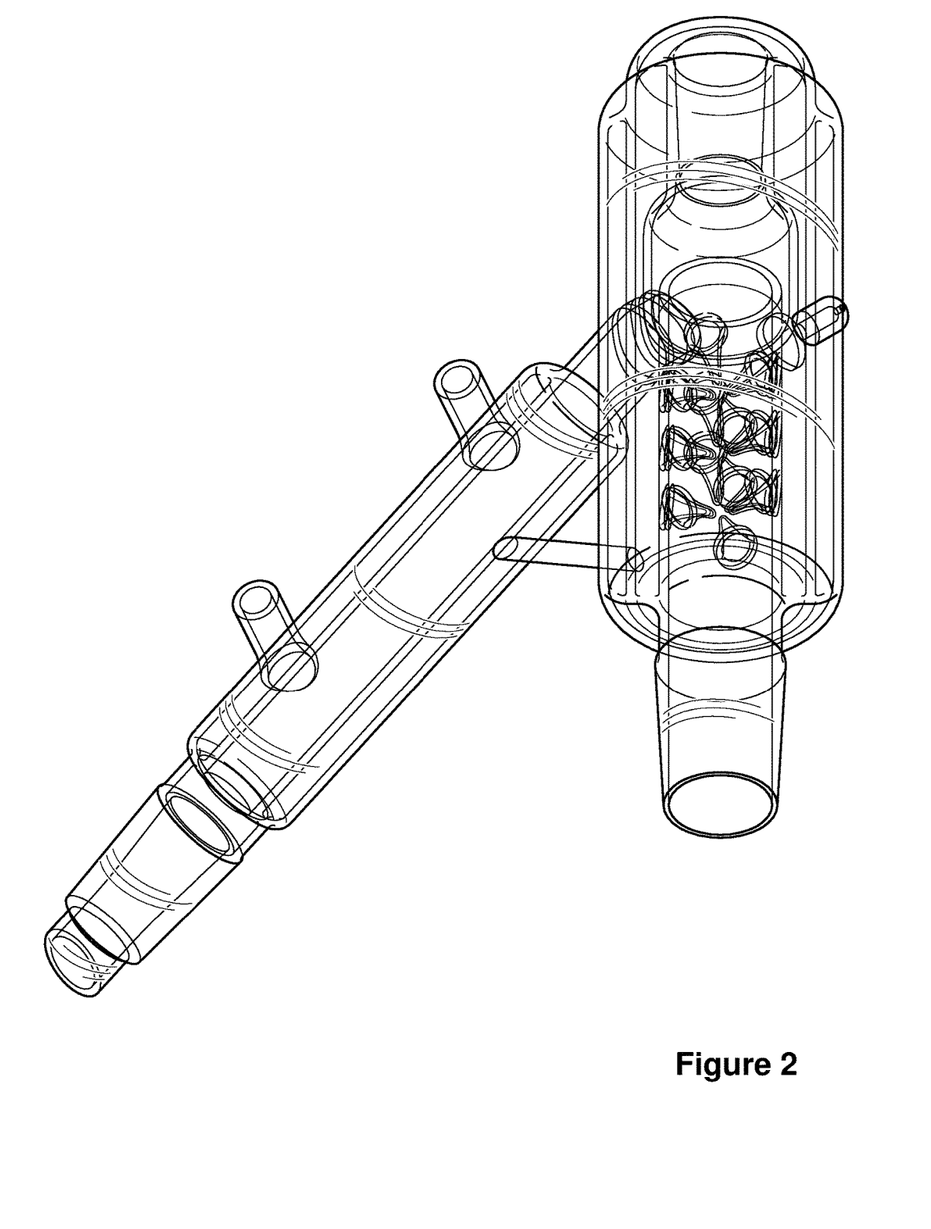
FIG. 2 shows a bottom and reverse side perspective view thereof.
Figure 3:
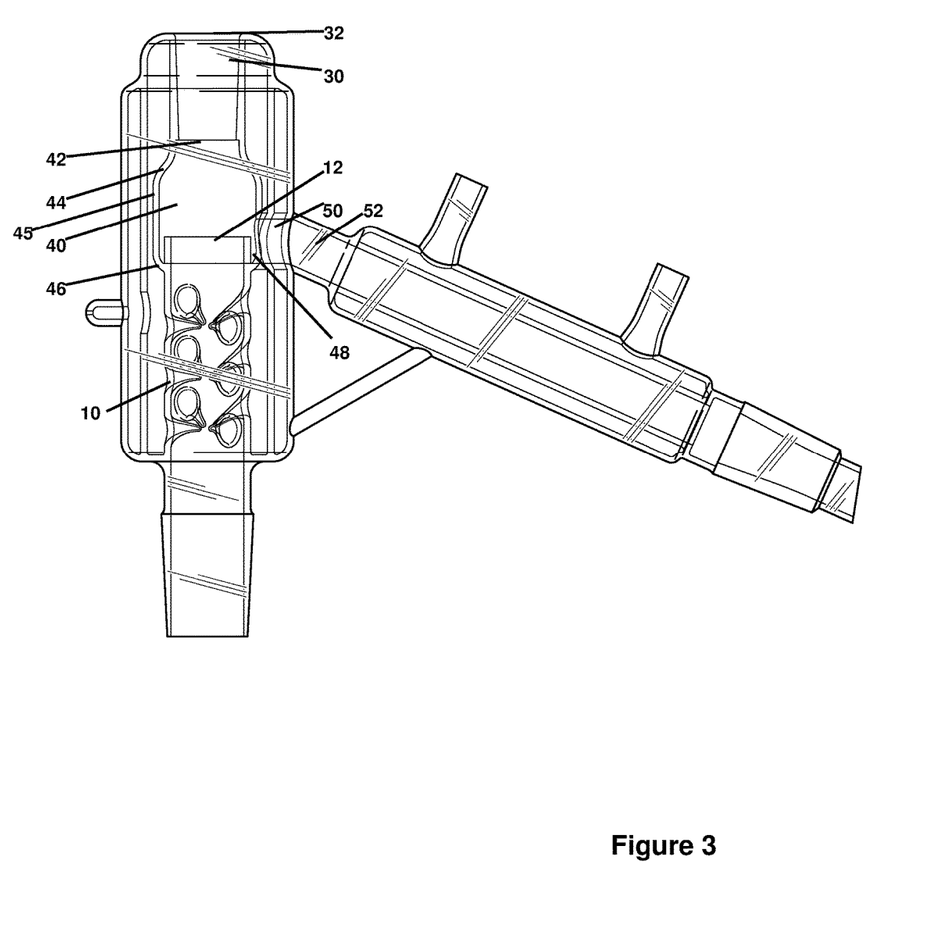
FIG. 3 shows a side view, the reverse side being a mirror image thereof.
Figure 4:
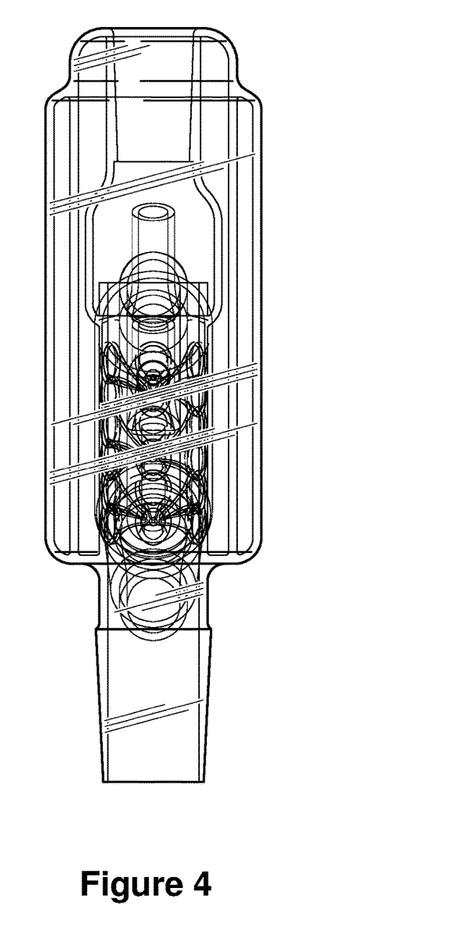
FIG. 4 shows a front view thereof.
Figure 5:
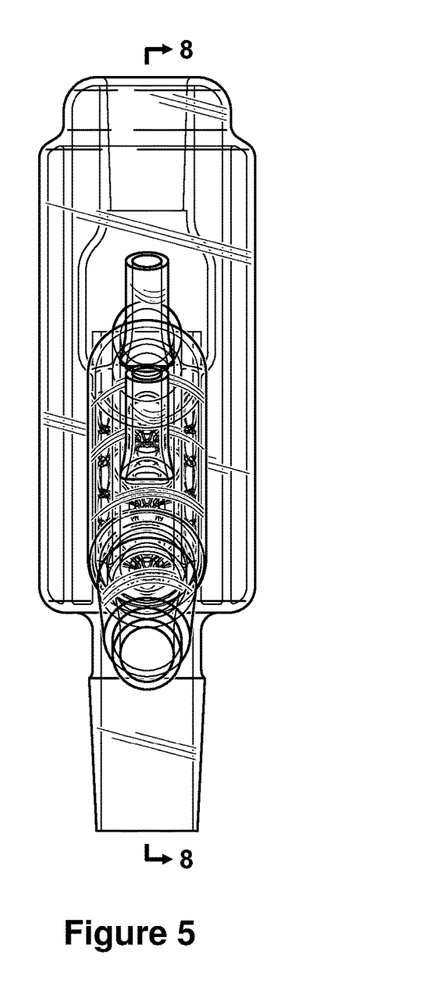
FIG. 5 shows a rear view thereof.
Figure 6:
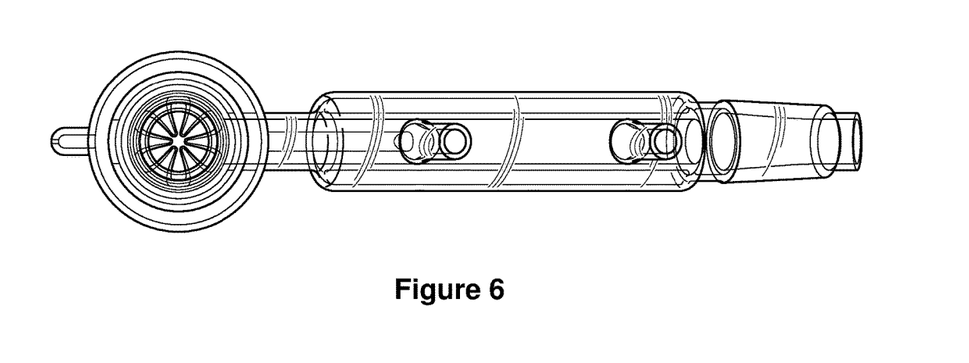
FIG. 6 shows a top plan view thereof.
Figure 7:
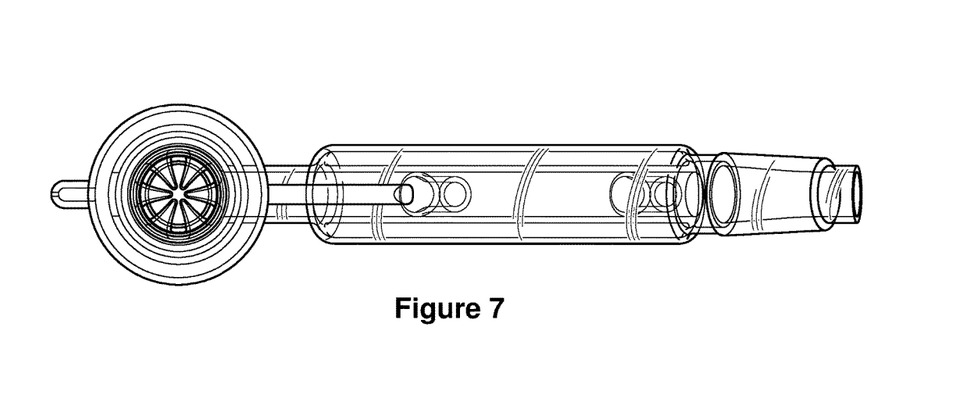
FIG. 7 shows a bottom plan view thereof.
Figure 8:
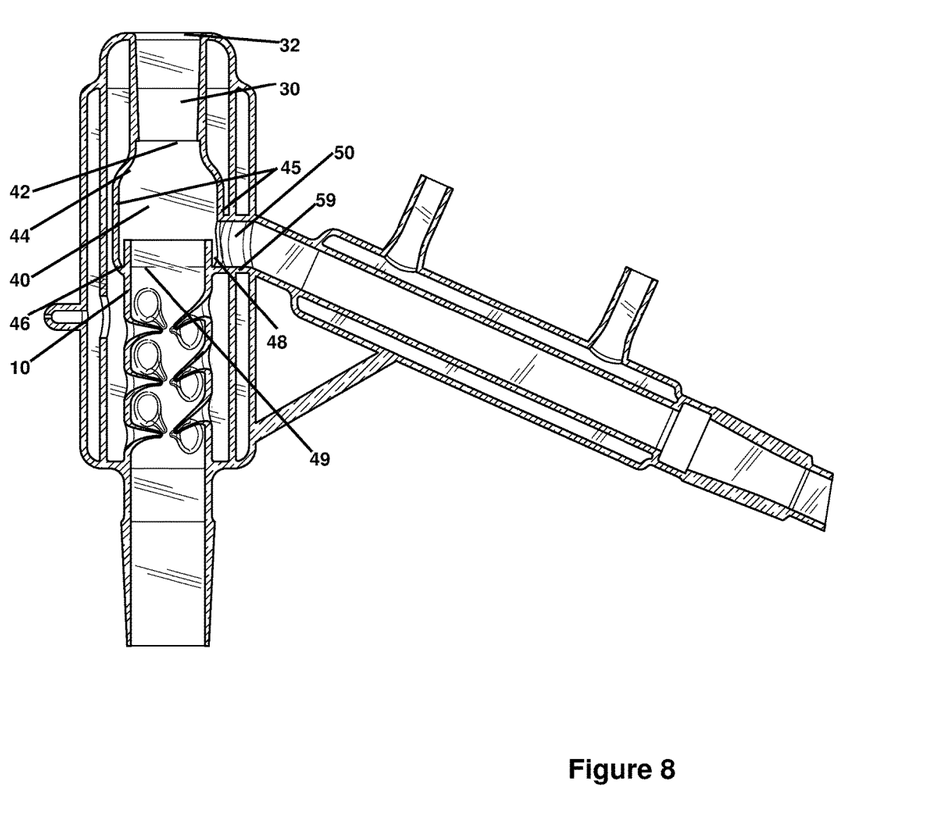
FIG. 8 shows a cutaway view of the side along section line 8-8 of FIG. 6.
Figure 9:
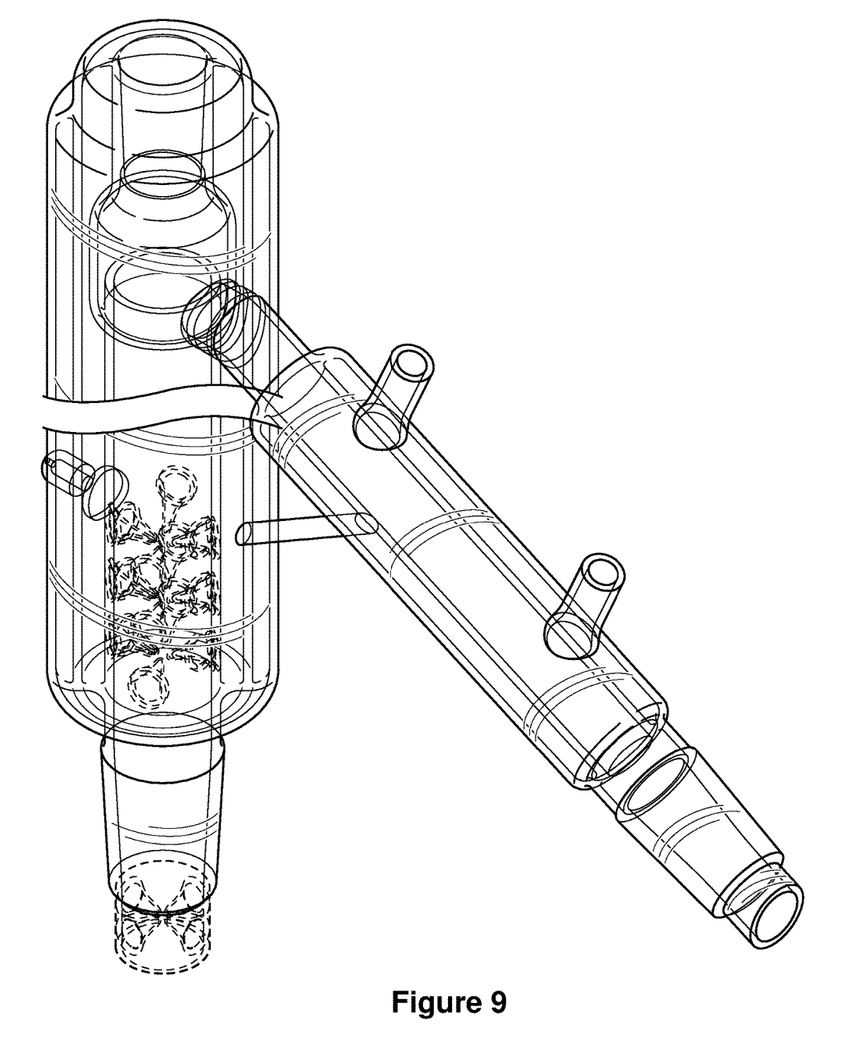
FIG. 9 shows another version of the distillation head of FIG. 1, having one of any height thereof.
Figure 10:
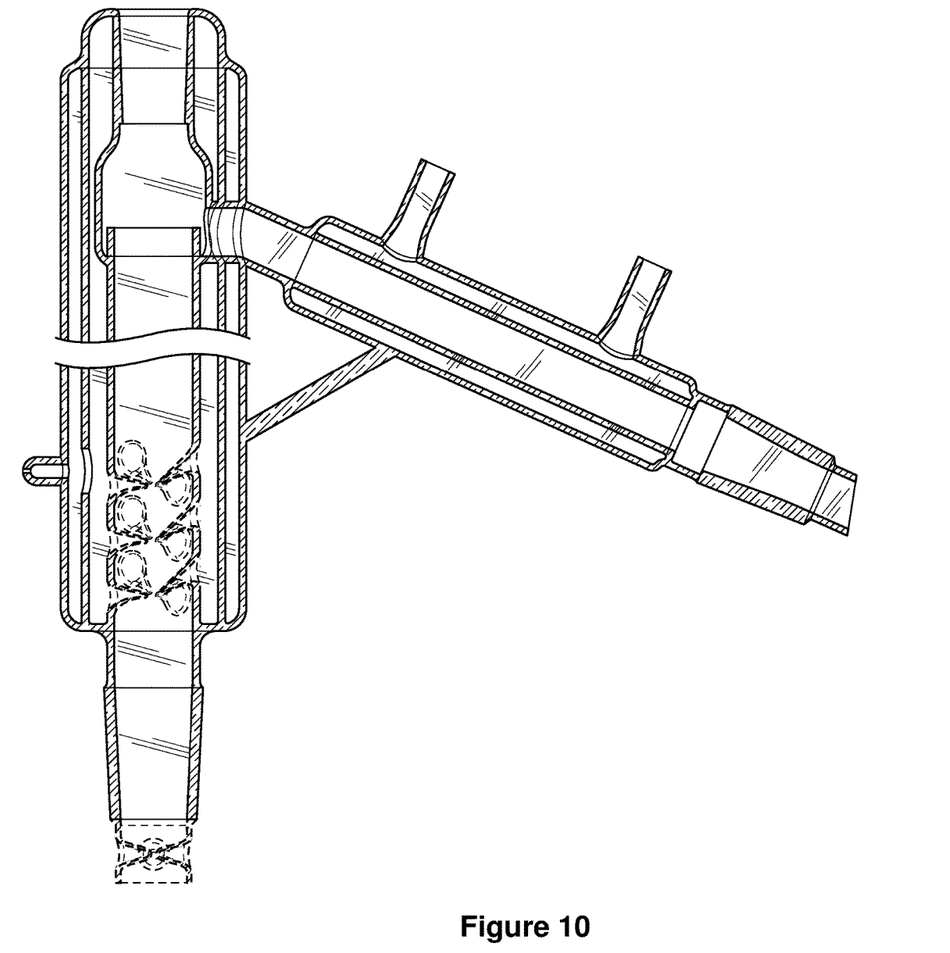
FIG. 10 shows a cutaway view of the side of FIG. 9 along section line 8-8 of FIG. 6.
Figure 11:
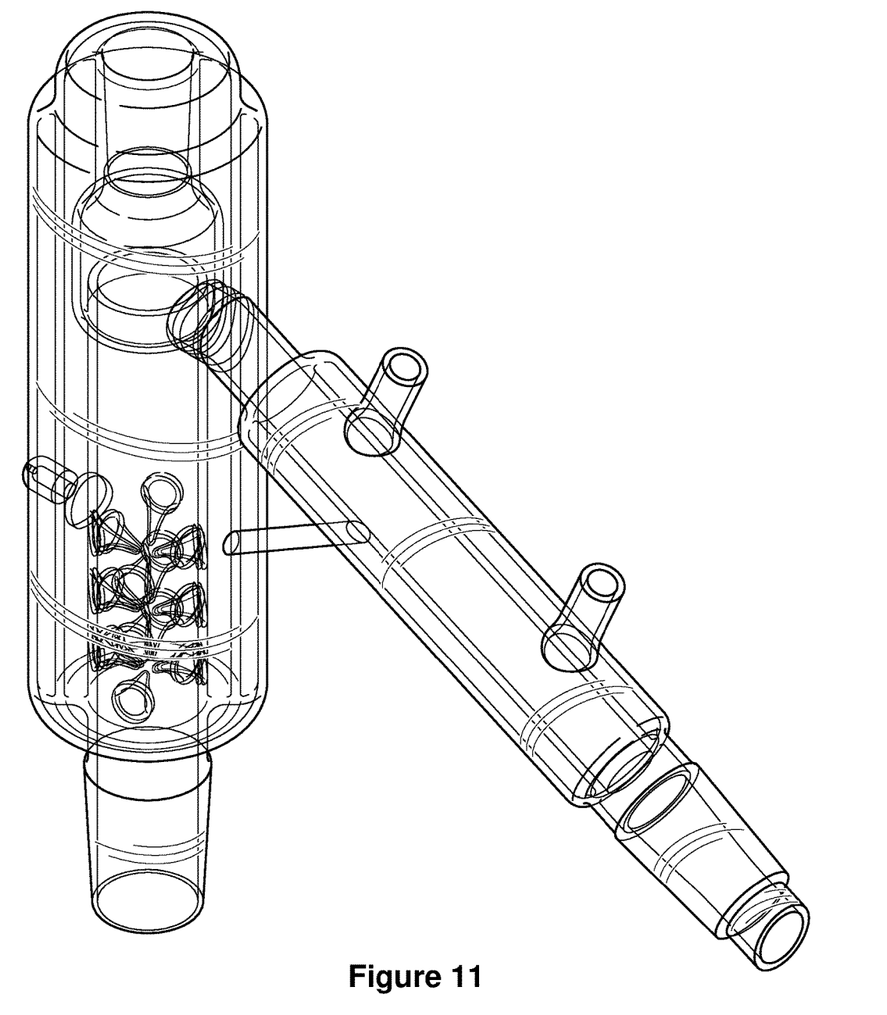
FIG. 11 shows a taller version of the distillation head of FIG. 1.
Figure 12:
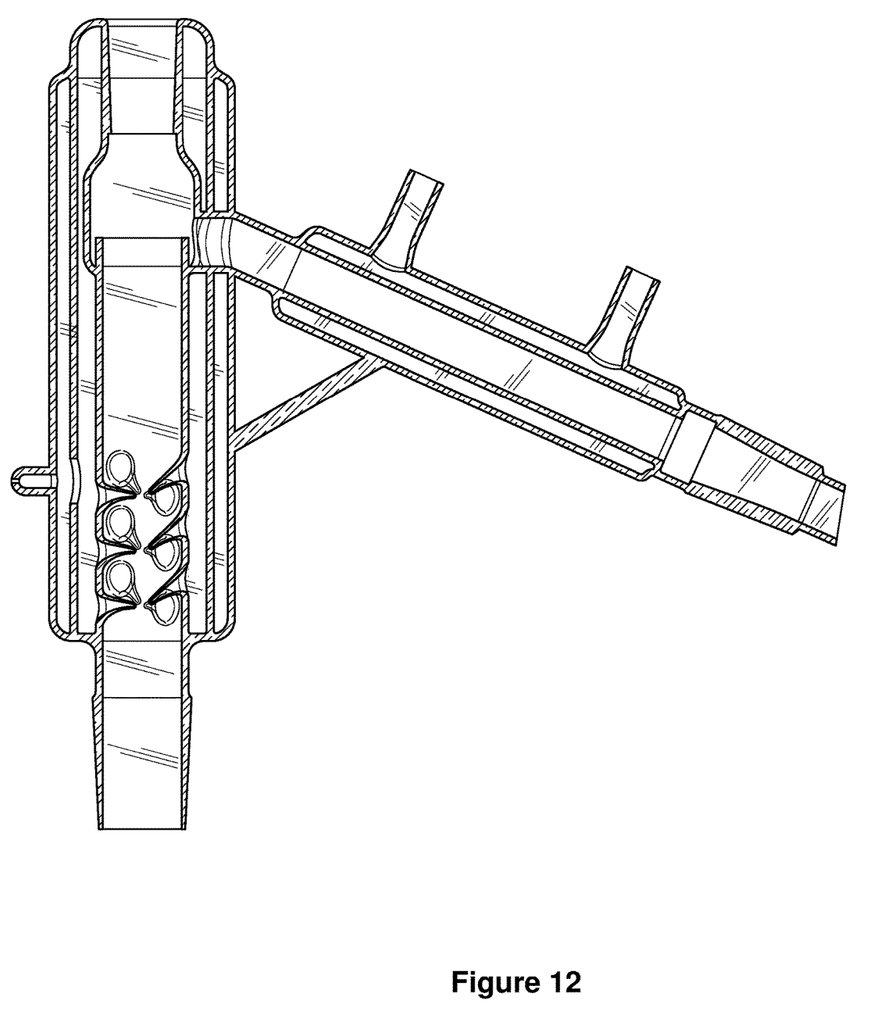
FIG. 12 shows a cutaway view of the side of FIG. 11 along section line 8-8 of FIG. 6.

The technology is best understood in view of the following discussion of the stages of distillation and figures. Discussing the figures simultaneously, FIG. 1 shows a top and side perspective view of a distillation head. FIG. 2 shows a bottom and reverse side perspective view thereof. FIG. 3 shows a side view, the reverse side being a mirror image thereof. FIG. 4 shows a front view thereof. FIG. 5 shows a rear view thereof. FIG. 6 shows a top plan view thereof. FIG. 7 shows a bottom plan view thereof. FIG. 8 shows a cutaway view of the side along section line 8-8 of FIG. 6. FIG. 9 shows another version of the distillation head of FIG. 1, having one of any height thereof. FIG. 10 shows a cutaway view of the side of FIG. 9 along section line 8-8 of FIG. 6. FIG. 11 shows a taller version of the distillation head of FIG. 1. FIG. 12 shows a cutaway view of the side of FIG. 11 along section line 8-8 of FIG. 6.

The distillation head 1 is connected to a condenser 200 or other devices through which distilled fractions (distillate) exits via a side exit region or portal 50 into the condenser upper region 52. A vertical tube 10 (or substantially vertical tube) is situated above material to be distilled which is heated such that vapors there-from rise up the vertical tube 10 into a fraction collector 40 (see also definition in the "summary" section).

The fraction collector 40 has an unencumbered/unobstructed interior which is free from blockage and open to passage of vapors and/or liquids there-through but for a top region 12 of the vertical tube 10 which extends above a plane defined by the bottom-most side 49 of the fraction collector 40. This bottom most plane (side) 49 is a horizontal plane in embodiments of the disclosed technology and is situated along, for example, the line in FIG. 3 which is horizontal and just below the top section 12 of the vertical tube 10, dividing a top section 12 of the vertical tube from the rest of the vertical tube 10. The bottom most extent of the fraction collector 40 can also be seen, for example, in FIG. 8 at a horizontal dashed line extending in line with a bottom 59 of the exit portal 50 as the exit portal 50 is in line with/has a lowest extent equal to that of the fraction collector 40 interior space. That is, the bottom side 49 of the fraction collector is at a same height as a bottom side 59 of the exit portal or exit region 50 are both horizontal in embodiments of the disclosed technology. The terms "horizontal" and "vertical" are used with reference to the "top" and "bottom" as described in the summary and/or with reference to how FIG. 8 is shown on the page and/or with reference to how the device is designed for use with vapors extending from the vertical tube 10 at a "bottom" until the fraction collector 40 which is mostly "above" the vertical tube 10.

The fraction collector 40, in embodiments of the disclosed technology, can be bulbous. This means that a central region thereof is wider than the at least a top portion thereof and in some embodiments, also a bottom portion thereof. There can be a combination of a straight vertical walls and curvilinear walls. In one such embodiment, there is a vertical wall 45 above a curvilinear lower side wall 46 and curvilinear upper side wall 44, the length of the lower side wall 46 being less than that of the upper side wall 44. The rounded nature of the top and bottom regions of the side wall prevents vortexes and/or abrupt de-condensation at shape edges as each of the edges is somewhat rounded in the fraction collector excepting for the bottom side 49 which is used for condensation to gather there-on.

A top edge or top portal 42 which is vertically at the top of the fraction collector 40, opens into a vacuum portal region 30 and vacuum portal 32 of the vacuum portal region. A vacuum can be attached thereto to pull gas upwards and out of the distillation unit 1 while condensed vapors fall to the bottom of the fraction collector 40, along the bottom edge 49 in liquid form. Such liquid condensation exits through the side exit portal 50 by way of gravity. Continued warmer vapors extending up through the vertical tube 10 substantially or fully can prevent vapors from falling back down the vertical tube 10. Instead, the condensation takes place at the cooler sides and falls outside the vertical tube 10 on to the floor or bottom side 49 of the fraction collector 40.

Note that, in embodiments of the disclosed technology, the vacuum portal region 30/vacuum portal 32 is aligned with, or substantially aligned with, the lever vertical tube 10. In this manner, it is as if the vertical tube 10 is interrupted by the fraction collector 40 before continuing above the fraction collector 40, e.g. above the top portal 42 of the fraction collector.

As seen perhaps most easily in FIG. 3, the fraction collector interior space is defined by, in some embodiments of the disclosed technology, a bottom most side 49 (being solid glass or other solid material interrupted by a vertical tube 10), a top portal 42 and side walls 44, 45, and 46 extending there-between. A side exit portal 50 cuts into a portion of a side wall 46 and/or 45 for distillate to exit from the fraction collector. The vertical tube 10 extends into the interior space defined by, and as defined herein, the fraction collector 40 at a top section 12 thereof. This forms a condensation region 48 of the fraction collector 40 which is exterior to the vertical tube 10/12, lower than an upper most extent of the vertical tube 10/12, and within the fraction collector 40. In this condensation region 48 within the fraction collector 40 and exterior to the vertical tube 10 vapors which condense collect as liquids before exiting from the side portal, the side portal having a lower most extent aligned with the lower most extent of the fraction collector 40 as described above.

Referring now to FIG. 1 in specific, an entry portal region 20 is shown which attaches to a flask or other holder of a material (liquid, solid, or combination thereof) to be distilled in embodiments of the disclosed technology. The material being distilled passes upwards through the lower vertical tube 10, which, in embodiments, is inline with the entry portal region 20. In some embodiments, the lower vertical tube 10 has interior flanges 15 and/or Raschig rings to support or is packing material which allows for more even heating or the like. Vapors then extend further upwards and out of the lower vertical tube 10 into the fraction collector 40 which extends, and has an interior space which extends, around the lower vertical tube 10, a side exit portal 50, and a top portal 42. The side walls are vertical, curvilinear, linear, and/or a combination thereof. A vacuum can be applied to the vacuum portal 32, pulling gas, such as atmospheric air, upwards and aiding in the pull of vapors. The pull of the vacuum/suction is calibrated, in embodiments of the disclosed technology, to be less strong than required to pull vapors and/or pull liquid out of the distillation unit 1. Rather, the vapors cool in the fraction collector 40 and condense to the bottom of the fraction collector exterior to the lower vertical tube 10, as warmer vapors continue to rise (preventing condensation) directly above/out of the top side of the lower vertical tube 10. These condensed vapors, now liquid, exit through the side portal 50 and drop down into the condenser 200.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalence of the claims are to be embraced within their scope. Combinations of any of the methods, systems, and devices described herein-above are also contemplated and within the scope of the disclosed technology.

I claim:

1. A distillation head, comprising:
a vertical tube extending into a fraction collector;
said fraction collector having a side exit portal allowing fluid flow from said fraction collector to a condenser, said side exit portal being perpendicular to said vertical tube;
said fraction collector being free from obstruction other than said vertical tube forming a shelf therein.

2. The distillation head of claim 1, wherein said fraction collector has vertical side walls, said vertical side walls being interrupted by a section of curvilinear side walls.

3. The distillation head of claim 2, wherein said section of curvilinear side walls terminate adjacent to or above a top quarter of a total height of said vertical side walls.

4. The distillation head of claim 1, further comprising a top vacuum portal.

5. The distillation head of claim 4, wherein said top vacuum portal extends to an outside of said distillation head.

6. The distillation head of claim 1, wherein said fraction collector comprises bulbous side walls which curvilinearly extend into said vertical tube at a bottom side thereof and to a vacuum portal at a top side thereof.

7. The distillation head of claim 6, wherein said vertical tube extends into said fraction collector less than 25% by height.

8. A fraction collector comprising:
a horizontal bottom side;
a side wall having a combination of vertical and curvilinear portions;
wherein an interior space of said fraction collector is defined between said horizontal bottom side, said side wall, and a top side opposite said horizontal bottom side, and a vertical tube extends past said horizontal bottom side into said interior space of said fraction collector;
further comprising a side exit portal whose bottom-most extent is at said horizontal bottom side of said fraction collector and wherein said bottom-most extent has a second portal extending there-through.

9. The fraction collector of claim 8, further comprising a top portal at said top side, wherein a circumference of said vertical tube is equal to a circumference of said top portal, and said vertical tube and said top portal are aligned horizontally with each other.

10. A fraction collector forming a bulbous section between a vertical tube entering into a bottom side of said bulbous section and a top portal, said top portal being aligned with said vertical tube,
said bulbous section having side walls and a side exit portal that cuts into one of said side walls of said bulbous section, said side exit portal has a bottom side which is horizontal and continuous with said bottom side of said bulbous section.

11. The fraction collector of claim 10, wherein said top portal is formed from a piece of glass which is continuous with said bulbous section.

12. The fraction collector of claim 11, wherein said bottom side of said bulbous section curves into and is continuous with said vertical tube, said vertical tube extending both upwards and downwards past a point where said bulbous section meets said vertical tube.

13. The fraction collector of claim 10, wherein said vertical tube extends into said bulbous section at least 10% and no more than 40%, by height thereof.

14. A distillation head comprising:
- a fraction collector forming a unitary structure with a lower tube, said lower tube extending above a bottom side of said fraction collector;
- an exit portal on a side of said fraction collector;
  - wherein said exit portal extends to and is horizontally in line with said bottom side of said fraction collector.

15. The distillation head of claim 14, wherein said fraction collector is a single glass unit fixedly attached within said distillation head.

16. The distillation head of claim 15, wherein a space between a portion of said lower tube which is within an interior space of said fraction collector and side walls of said fraction collector is where vapors passing up through said lower tube are condensed into liquid before flowing through said exit portal.

\* \* \* \* \*